United States Patent [19]
Leavitt

[11] Patent Number: 5,779,731
[45] Date of Patent: Jul. 14, 1998

[54] BALLOON CATHETER HAVING DUAL MARKERS AND METHOD

[75] Inventor: Ernest E. Leavitt, Coral Springs, Fla.

[73] Assignee: Cordis Corporation, Miami, Fla.

[21] Appl. No.: 770,875

[22] Filed: Dec. 20, 1996

[51] Int. Cl.⁶ .................................................. A61M 29/00
[52] U.S. Cl. ............................... 606/194; 606/198; 623/1; 623/12; 604/96
[58] Field of Search ........................... 606/191, 192, 606/194, 195, 198, 200; 604/95–101; 623/1, 12

[56] References Cited

U.S. PATENT DOCUMENTS

| | | |
|---|---|---|
| 4,571,240 | 2/1986 | Samson et al. |
| 4,811,737 | 3/1989 | Rydell .................. 606/194 |
| 4,819,751 | 4/1989 | Shimada et al. ......... 606/194 |
| 4,906,244 | 3/1990 | Pinchuk et al. |
| 4,938,220 | 7/1990 | Mueller, Jr. |
| 5,108,415 | 4/1992 | Pinchuk et al. |
| 5,135,535 | 8/1992 | Kramer .................. 606/194 |
| 5,156,612 | 10/1992 | Pinchuk et al. |
| 5,223,205 | 6/1993 | Jackowski et al. |
| 5,236,659 | 8/1993 | Pinchuk et al. |
| 5,290,306 | 3/1994 | Pinchuk et al. |
| 5,304,197 | 4/1994 | Pinchuk et al. |
| 5,356,591 | 10/1994 | Pinchuk et al. |
| 5,370,615 | 12/1994 | Johnson. |
| 5,449,371 | 9/1995 | Pinchuk et al. |
| 5,478,320 | 12/1995 | Trotta. |
| 5,558,643 | 9/1996 | Samson et al. .......... 606/194 |

*Primary Examiner*—Michael Buiz
*Assistant Examiner*—William W. Lewis
*Attorney, Agent, or Firm*—Michael W. Montgomery

[57] ABSTRACT

An intravascular balloon catheter has a balloon near the distal end of a catheter shaft and a pair of radiopaque markers positioned within the balloon interior. The distal marker is disposed on an inner shaft member, and the proximal marker is disposed at the distal end of an outer shaft member. The markers may be positioned to indicate under fluoroscopy the position and working length of the balloon.

31 Claims, 6 Drawing Sheets

FIG. 3
FIG. 4
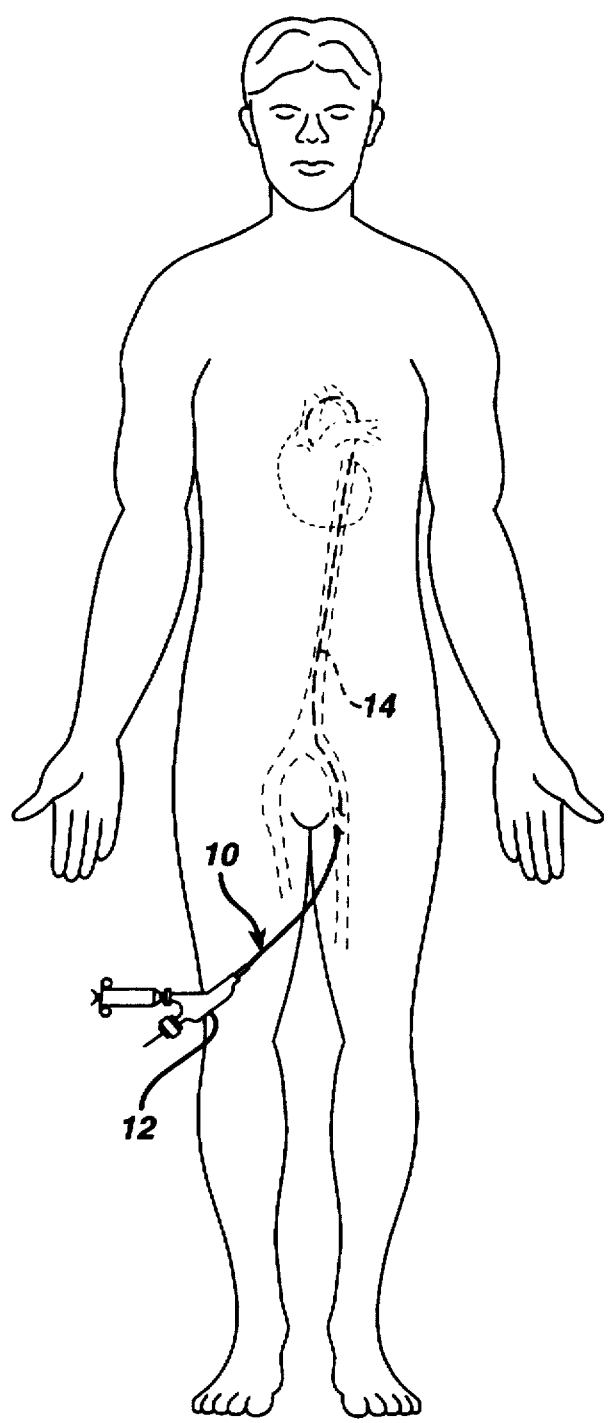
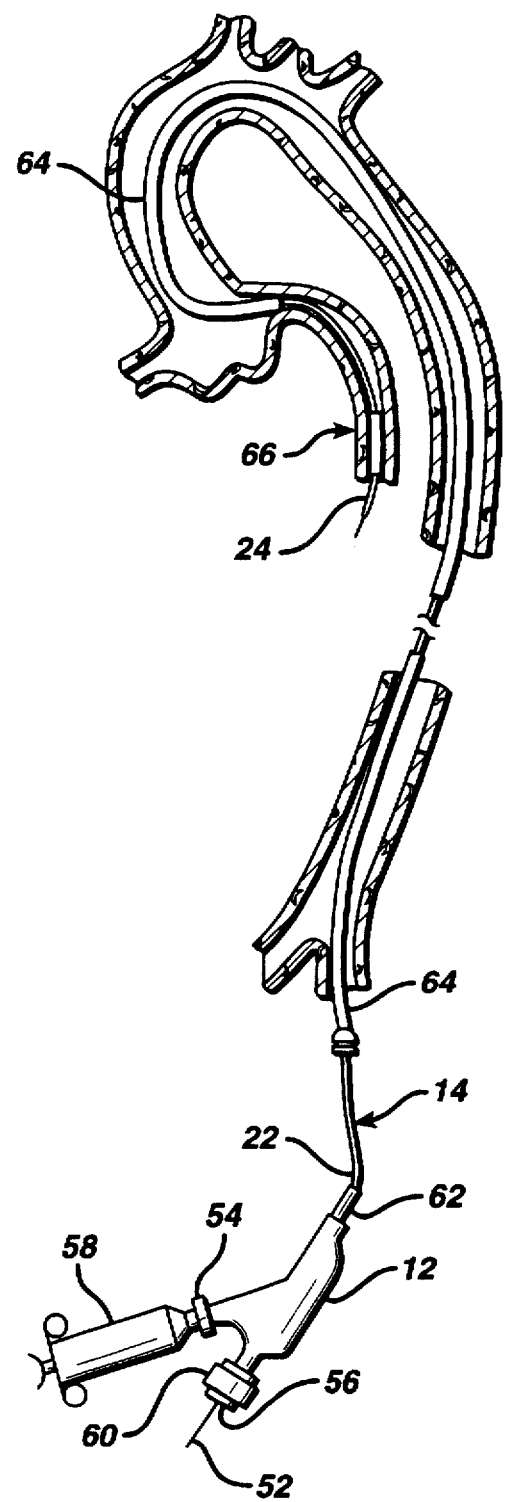

BALLOON CATHETER HAVING DUAL MARKERS AND METHOD

BACKGROUND AND DESCRIPTION OF THE INVENTION

This invention relates generally to the field of intravascular catheters, and more particularly to a balloon catheter having dual markers.

Intravascular catheters for advancement into the blood vessels of a patient are presently in wide clinical use. Many clinical applications exist for such catheters, including diagnostic and interventional procedures. Diagnostic procedures include angiography, in which a catheter is advanced along a selected vascular path until a distal tip of the catheter is located at the desired site. A liquid dye is then injected from a proximal hub outside the patient's body, through an infusion lumen, and out the catheter distal tip. This dye is radiopaque, so that its flow through the blood vessels can be visualized on a fluoroscopy system.

Interventional procedures include any treatment or therapy, as opposed to diagnosis, using an intravascular catheter having an interventional device to cause a change in the blood vessel. The most common interventional device is a dilatation balloon, which can be expanded within a narrowing or obstruction of a blood vessel or other body passageway to increase blood flow or otherwise treat the diseased region. One advantage of using a balloon catheter to treat an area of a patient's vascular system is to avoid the difficulties associated with performing surgery.

For example, in a typical balloon angioplasty procedure, a partially or fully occluded blood vessel lumen is enlarged and reopened to allow greater blood flow. A balloon catheter is introduced percutaneously into the vascular system and advanced along the desired path until the balloon reaches the site of the obstruction or constriction, called a stenosis. Once so positioned, the balloon is then expanded in the stenosis by inflating it with an inflation fluid, to dilate the vessel lumen and facilitate greater blood flow. Afterwards, the balloon is deflated, and the catheter is removed from the patient. Examples of such procedures are coronary angiography and angioplasty, often referred to as percutaneous transluminal coronary angioplasty (PTCA). Of course, the present invention may be utilized in any application to which it is suitable.

Generally, balloon catheters are constructed of a flexible shaft, a hub affixed to a proximal end of the shaft, and a small inflatable balloon, usually located at or near a distal tip of the catheter shaft. The balloon can be inflated by supplying a pressurized inflation fluid through an inflation port on the hub, which communicates with an inflation lumen defined by the catheter shaft, enabling the inflation fluid to flow through a distal end of the inflation lumen into the interior volume of the balloon. The balloon is often made of a flexible, relatively inelastic material. This inelastic material is preferably capable of imposing pressures of several atmospheres to expand the stenosis, without becoming too large within the vessel. Likewise, the balloon may be deflated so the catheter can be withdrawn by pulling a partial vacuum on the inflation fluid at the inflation port.

In operation, the balloon catheter must be advanced along a specific path, until the balloon is positioned precisely within the stenosis. Of course, the physician cannot see most of the catheter. As a result, the physician navigates the catheter along the desired path by using fluoroscopy, often referred to as an X-ray machine. To assist the physician in guiding the catheter, portions of the catheter may be formed of radiopaque materials, which are highly visible on a fluoroscope. For example, the catheter shaft may incorporate a plastic formulation loaded with a radiopaque agent or filler. Likewise, one or more radiopaque metal marker bands may be affixed to the catheter shaft in various positions, such as inside the balloon, or at the distal tip.

Prior to beginning the catheterization, a guiding catheter is advanced through the vascular system until its distal tip is located at the entrance to the desired smaller branching vessels. The guiding catheter acts as a conduit through which various diagnostic or interventional catheters can be advanced. A type of radiopaque catheter which can be used to make a guiding catheter is disclosed in U.S. Pat. No. 5,171,232 to Castillo et al., entitled "Catheter Having Highly Radiopaque, Flexible Tip," the disclosure of which is hereby incorporated by reference.

In addition, the balloon catheter may be constructed as a "fixed wire" catheter, in which the distal end of the inner shaft member is affixed to a distally extending flexible wire. Otherwise, the balloon catheter may be provided with a guidewire lumen, forming a sleeve through which a guidewire can be inserted, advanced, and withdrawn. Guidewires are described in U.S. Pat. No. 4,846,186 to Box et al., entitled "Flexible Guidewire," the disclosure of which is hereby incorporated by reference. The guidewire lumen should have a lubricious inner surface, to facilitate easy movement of the balloon catheter along the guidewire.

In a balloon catheter, guidewire lumen types may be classified in two general categories. The first type is referred to as an "over the wire" balloon catheter arrangement, which means that the catheter is advanced over a guidewire which passes through a guidewire lumen extending along the entire length of the catheter shaft. This type of guidewire lumen traverses from a distal port at the catheter distal end to a proximal port on the hub. However, it is often desirable to remove a previously inserted balloon catheter and exchange it for another, without also removing the guidewire. One solution to this problem is to construct a balloon catheter having the second type of guidewire lumen, referred to as a "rapid exchange" configuration. This configuration includes a relatively short guidewire lumen, so that a single operator may withdraw and exchange a first balloon catheter while holding the guidewire in place by grasping a portion of the guidewire that is outside of and parallel to the proximal catheter shaft. A second rapid exchange balloon catheter can then be advanced over the guidewire in a similar manner.

There are also two general categories of balloon catheter shafts. The first type defines the inflation lumen and guidewire lumen in a side by side and parallel arrangement, often referred to as a "dual lumen" catheter. This type of shaft is usually formed by a single tubular extrusion. In contrast, the inflation lumen and guidewire lumen are arranged coaxially in the second type of catheter shaft, often called a "coaxial lumen" catheter. In a coaxial lumen catheter, the balloon guidewire is threaded down the inner passage, which forms the guidewire lumen, and the inflation fluid is injected into the balloon via an outer annular passage defined between the outer surface of an inner guidewire tube and an inner surface of an outer tube, which forms the inflation lumen.

The balloon itself is often formed having a central cylindrical portion between a pair of tapering segments. The central portion has a diameter that is carefully selected to match the size of the body vessel. The central portion also defines an effective or working length, and it is desirable to fluoroscopically indicate the precise location of this working length.

A common feature used to give some indication of the balloon's position is a marker band in the center of the balloon working length. Marker bands are made of a radiopaque material such as platinum. The marker band is then assembled on the catheter by slipping it onto the inner shaft member and affixing it in position with an adhesive or by slightly heating the plastic inner shaft.

Since it is desirable to more accurately indicate the position of the effective portion of the balloon in the patient's body, the position of the working length is preferably indicated by a pair of separate marker bands. Referring to the drawings, the prior art balloon catheter 200 shown in FIG. 5 has a balloon 202, an inner and outer shaft member 204 and 206, and a proximal and distal marker band 208 and 210. The balloon 202 and outer shaft 206 are each manufactured separately. Likewise, inner shaft member 204 is also made separately, and marker bands 208 and 210 are affixed to the inner shaft 204 in isolation from the other components, thus forming an inner shaft subassembly 212. The marker bands 208 and 210 are thus both permanently affixed to the same inner shaft 204 before the remainder of the balloon catheter 200 is assembled.

However, in the balloon catheter 200 illustrated in FIG. 5, marker bands 208 and 210 have been affixed to the inner shaft member 204 such that they fail to match with the proximal and distal ends 214 and 216 of the balloon working length 218. There are several possible reasons for such a mismatch, including the tolerances on the positions of both marker bands 208 and 210 and the tolerance on the balloon working length 218. The process for blowing and forming the balloon 202, including heat treatments of the balloon 202, can slightly alter its length.

It should be apparent that the elements of catheter 200 shown in FIG. 5, namely the balloon 202, outer shaft 206, and inner shaft subassembly 212, cannot be assembled so that both marker bands 208 and 210 are aligned with the ends 214 and 216 of the working length 218. Only one of the marker bands 208 and 210 can be positioned correctly, but the other will not match. Because of this misalignment, the particular balloon catheter 200 shown in FIG. 5 would be scrapped. In fact, it is so important that the marker bands 208 and 210 be exactly positioned, that the tolerance for the proximal and distal marker band locations can be as narrow as +/-0.0025 inches.

It is therefore desirable to be able to customize the relative positions of the markers during assembly, so as to precisely align them longitudinally with the ends of the balloon working length, thereby increasing yields during manufacture. Because it is not feasible to individually tailor the positions of two markers after they have been affixed to a single shaft member, an unacceptable percentage of balloon catheters may need to be scrapped if the markers fail to exactly match both ends of the balloon working length. In other words, an operator may assemble a balloon onto a catheter shaft, only to discover that either one marker, but not both, can properly be aligned with the balloon.

In accordance with the novel balloon catheter design of the present invention, an intravascular balloon catheter is provided having an improved arrangement of dual markers to precisely indicate the balloon working length. This unique arrangement enables the relative positions of the proximal and distal markers to be customized during assembly, to exactly match the balloon working length. In other words, the method and apparatus of the present invention compensates for the tolerances on the various components. According to a preferred embodiment of the present invention, a proximal marker is affixed to a distal end of an outer shaft tube of a balloon catheter shaft, rather than an inner shaft member. In contrast, a distal marker is affixed to the inner shaft member, near its distal end. As a result, the relative positions of the markers can be adjusted and customized to the exact working length of a particular balloon by adjusting the longitudinal positions of the inner and outer shafts.

This precise alignment results from assembling the balloon catheter according to the method of the present invention. First, the proximal and distal radiopaque markers are affixed to the outer and inner shaft members, respectively. Second, the proximal end of the balloon is then sealed to the outer shaft member, while the proximal marker and the proximal transition are aligned. Third, the inner shaft member is inserted within the tubular outer shaft, and the distal marker affixed to the inner shaft is aligned with the distal end of the balloon working length. Fourth, the balloon distal end is sealed to the inner shaft member, such that the distal marker is longitudinally aligned with the distal end of the balloon working length. As a result, the position of both markers is easily adjusted to match the actual balloon working length.

These and various other objects, advantages and features of the invention will become apparent from the following description and claims, when considered in conjunction with the appended drawings.

BRIEF DESCRIPTION OF THE DRAWINGS

FIG. 3 is a diagrammatic view of a balloon catheter system assembled in accordance with this invention, in use within the body of a patient;

FIG. 4 is a perspective view of a balloon catheter system according to this invention, showing a partial cross-section of the patient's vascular system;

DETAILED DESCRIPTION OF SPECIFIC EMBODIMENTS

Figure 1:
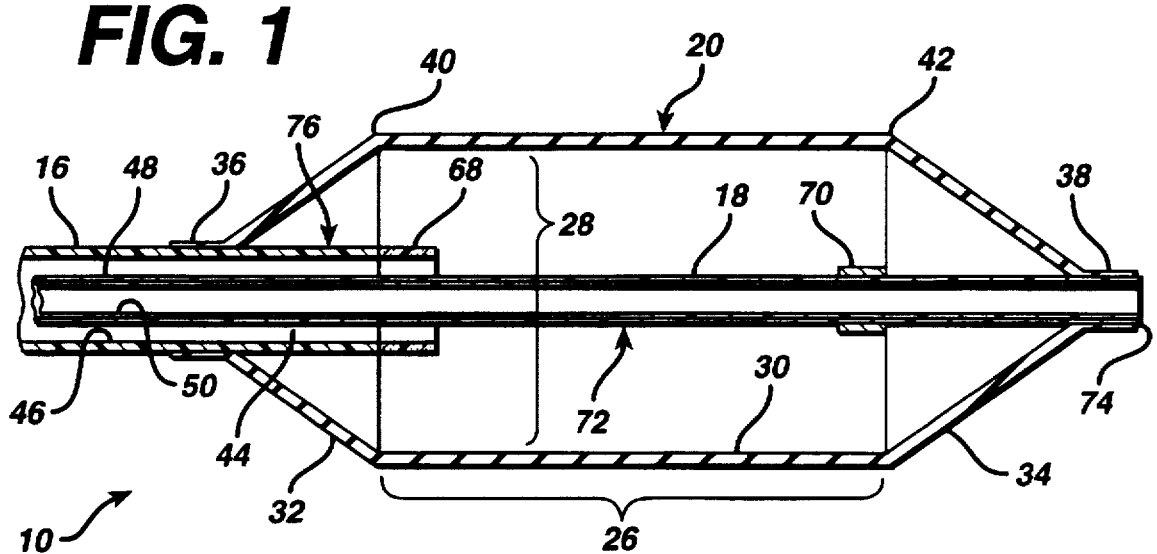
FIG. 1 is a partial cross-sectional view of a balloon catheter arranged according to the principles of the present invention.

The following description of the preferred embodiments of the present invention is merely illustrative in nature, and as such it does not limit in any way the present invention, its application, or uses. Numerous modifications may be made by those skilled in the art without departing from the true spirit and scope of the invention.

With reference to the drawings, the balloon catheter of the present invention is generally designated by reference numeral 10. Balloon catheter 10 has a hub 12, a catheter shaft 14 constructed of an outer shaft member 16 and an inner shaft member 18, and a dilatation balloon 20. The hub 12 is affixed to the proximal end 22 of balloon catheter 10, while the balloon 20 is near the catheter distal end 24. Balloon 20 is preferably formed of a flexible, substantially inelastic material and defines a predetermined working length 26 and inflated diameter 28. These dimensions are used by physicians to carefully select a balloon having the proper size and effective length for each patient's anatomy.

The balloon 20 preferably has a central working portion 30, a proximal and distal frusto-conical or tapering segment 32 and 34, and a proximal and distal leg 36 and 38. A proximal and distal transition point 40 and 42 are each defined where the central working portion 30 meets the proximal and distal tapering segments 32 and 34, respectively. The transitions 40 and 42 define the proximal and distal ends of the balloon working length 26. The proximal and distal legs 36 and 38 are sealed to the outer and inner shaft member 16 and 18, respectively, preferably by heat sealing.

Figure 2:
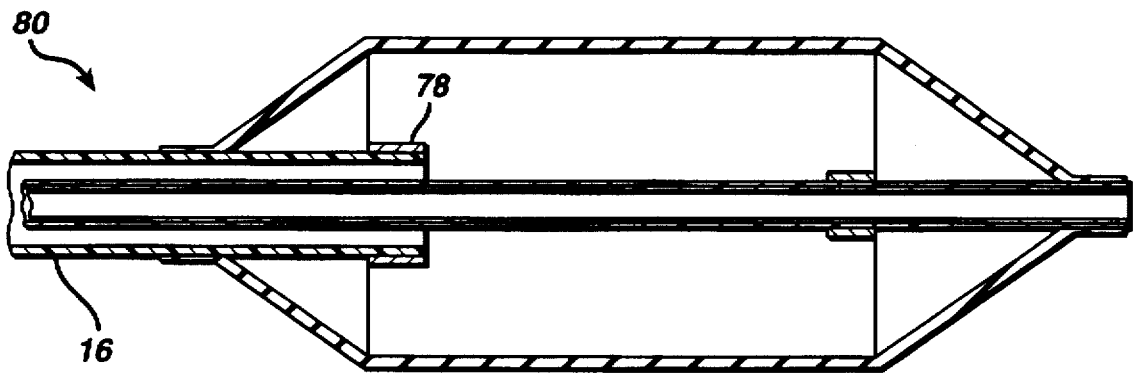
FIG. 2 is a partial cross-sectional view of another balloon catheter according to this invention.

According to the preferred embodiment, the outer and inner shaft members 16 and 18 are both tubes, as illustrated in FIGS. 1 and 2. An inflation lumen 44 is defined by a generally annular space between the inner and outer surfaces 46 and 48 of the outer and inner shaft members 16 and 18, respectively. Inner shaft member 16 defines a guidewire lumen 50 for slidingly receiving a guidewire 52. The guidewire 52 is used in conjunction with the balloon catheter 10 to assist in steering and navigating the balloon catheter 10 along the desired vascular path, so that the balloon 20 reaches the diseased location. The outer surface of outer tube 16 may of course be treated or coated to improve the performance of the balloon catheter 10, such as by applying a hydrophillic or other type of coating.

Hub 12 is a Y-connector having an inflation port 54 in fluid communication with inflation lumen 44, and a guidewire port 56 communicating in conventional manner with guidewire lumen 50. Inflation port 54 is adapted to be connected by a luer-lock coupling with a source of pressurized inflation fluid, such as syringe 58. Inflation lumen 44 extends from inflation port 54 along the catheter between catheter tubes 16 and 18, and terminates in communication with the interior of balloon 20. Guidewire port 56 has a hemostatic valve 60 through which the guidewire 52 can pass, without allowing blood to leak from hub 12. Hub 12 preferably has a tubular strain relief 62 to resist kinking by the catheter shaft 14 at its proximal end 22. Preferably, hub 12 can be made by injection-molding it around catheter shaft 14.

Balloon catheter 10 is illustrated in use within the vasculature of a patient in FIGS. 3 and 4, with a guidewire 52, syringe 58, and a guiding catheter 64. Balloon 20 is disposed within a stenosis 66, which will be expanded as balloon 20 inflates. Since the balloon catheter 20 can be successfully used without surgery, the physician never sees the cross-sectional view of FIG. 4. Rather, the physician must rely on a murky fluoroscope image. It is very important that the physician be able to discern from that image, exactly where the effective balloon length is located in the patients body.

In accordance with the present invention, balloon catheter 10 incorporates a novel arrangement of a pair of radiopaque markers for precisely indicating the location of the balloon working length 26. The markers are disposed within the interior of the balloon 20, and are positioned along the longitudinal axis of the balloon at the exact position of the proximal and distal transitions. As shown in the embodiment of FIG. 1, this unique arrangement enables the relative positions of proximal and distal markers 68 and 70 to be customized during assembly of the balloon catheter 10. The present invention thereby compensates for any variances in component dimensions or manufacturing tolerances present in the components. Accordingly, the distal marker 70 is affixed to the inner shaft 18, yet the proximal marker 68 is affixed to the outer shaft 16. This enables the distance between the two markers 68 and 70 to be adjusted to precisely match the working length 26 of a particular balloon 20.

Balloon catheter 10 is assembled by the method of the present invention, as illustrated in FIGS. 11–14. Inner shaft 18 is extruded in the form of a tube, and distal marker band 70 is affixed to inner shaft 18 near its distal end 24, to form inner shaft subassembly 72. The position of distal marker band 70 is selected appropriate to the approximate dimensions of the type of balloon 20 to be used, and is preferably spaced from the inner shaft distal end 24 a distance approximately equal to the longitudinal length of distal balloon tapering segment 34, plus the length of distal leg 38, plus any desired length of inner shaft distal tip 74. Also, outer tubular shaft 16 is extruded in the form of another tube having a larger diameter than inner shaft 18, and proximal marker 68 is affixed to outer shaft 16 preferably at its distal end, forming outer shaft subassembly 76. Balloon 20 is formed according to conventional processes, including for example, those disclosed in U.S. Pat. No. 5,304,197 to Pinchuk et al., entitled "Balloon For Medical Devices And Fabrication Thereof," the disclosure of which is hereby incorporated by reference. Of course, balloon 20 as well as inner and outer shaft subassemblies 72 and 76 may be manufactured simultaneously or in whatever desired order, or even in separate facilities.

Then, a balloon catheter 10 is assembled of a particular balloon 20 with a particular inner and outer shaft subassembly 72 and 76. These subassemblies 72 and 76 are brought together for the first time at this stage, and it is not practicable to do so earlier. In addition, it is not practicable to attempt to precisely place a pair of markers 68 and 70 on an inner shaft 18 to match the working length 26 of a specific actual balloon 20, and too expensive then to keep that particular balloon 20 together with that inner shaft 18 as the subassemblies 72 and 76 are transported to the final assembly area.

Figure 5:
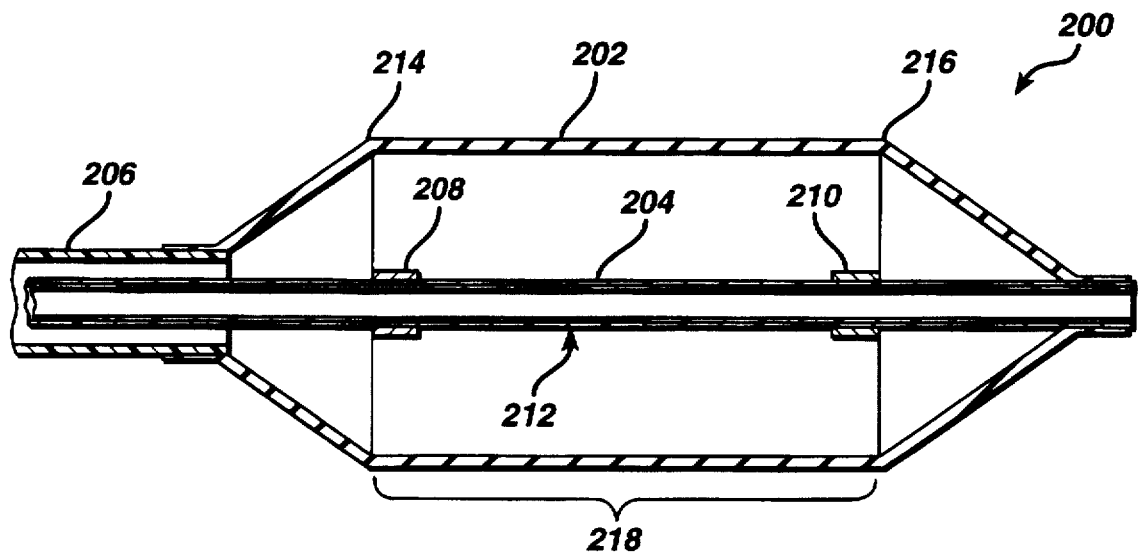
FIG. 5 is a partial cross-sectional view of a balloon catheter according to the prior art.

According to the present invention, balloon catheter 10 has a proximal marker 68 affixed to a distal end of outer shaft 16, instead of inner shaft 18. As a result, proximal marker 68 may be precisely aligned to match the proximal balloon transition 40, by shifting the relative positions of inner and outer shafts 18 and 16 before sealing balloon 20 thereto. In contrast with the prior art balloon catheter 200 illustrated in FIG. 5, outer shaft tube 16 extends further distally within the interior of the balloon 20. Of course, outer shaft 16 preferably extends distally just enough to align the proximal marker 68 in the correct position, to enhance the flexibility of the distal end of the catheter 10.

Various arrangements of the present invention are possible. According to the present invention, proximal marker 68 may be made as a plastic formulation incorporating a radiopaque filler agent, as illustrated in FIG. 1. Such a marker 68 has several advantages, among which is that it is flexible. Indeed, proximal marker 68 can be made even more flexible than outer and inner shaft members 16 and 18, so as to be less traumatic when advanced through vasculature. Moreover, the percentage of radiopaque filler in the plastic formulation of proximal marker 68 can be tailored to a desired degree of radiopacity. Preferably, the radiopacity of proximal marker 68 may be selected so that the proximal and distal markers 68 and 70 are equally bright when viewed on a fluoroscope. Without this tailoring capability, the proximal marker 68 might appear brighter on the fluoroscope than distal marker 70, because it has a larger diameter and correspondingly larger size.

Figure 8:
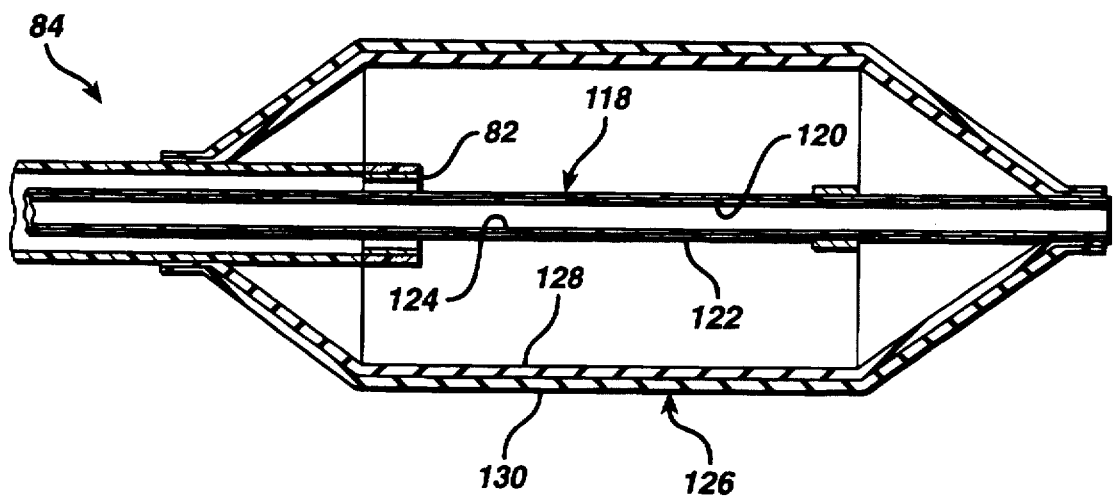

In the alternative, the proximal marker may be a metal marker band 78 affixed to outer tubular shaft 16, as depicted in the balloon catheter 80 FIG. 2. Further, proximal metal marker band 78 may be disposed around the outside of outer tube, as illustrated in FIG. 2, or a metal proximal marker band 82 may be inserted within the lumen of outer tube 16, as shown in FIG. 8. Such an interior marker band configuration exhibits a smoother exterior surface, and may reduce the profile of the balloon catheter 84.

Figure 10:
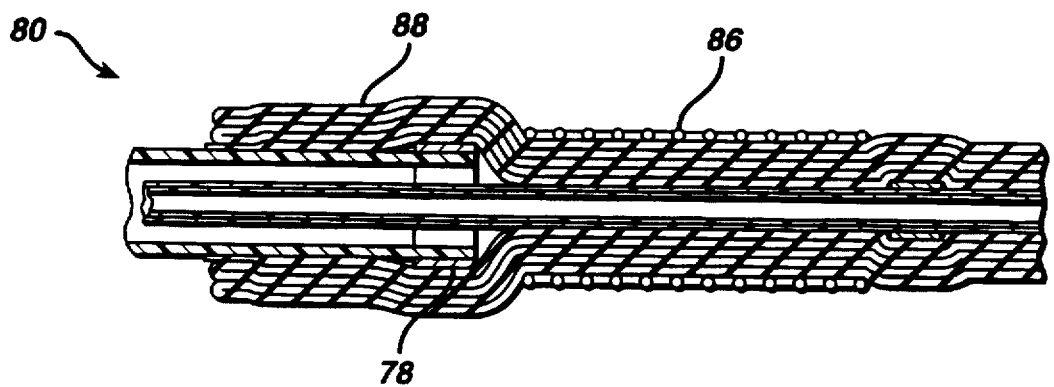
FIG. 10 is a partial cross-sectional view of another alternative embodiment of this invention, showing a stent crimped around a deflated balloon.
Figure 11:
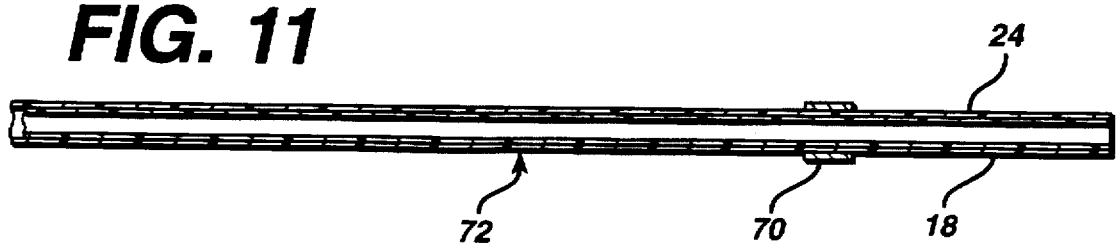
FIGS. 11–14 are partial cross-sectional views of component parts and subassemblies of a balloon catheter during a method of manufacturing a balloon catheter according to this invention.
Figure 12:
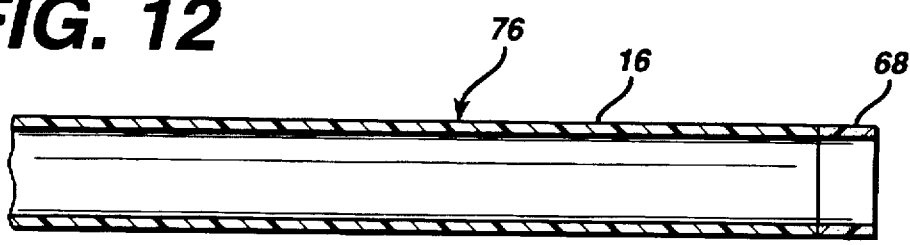
Figure 13:
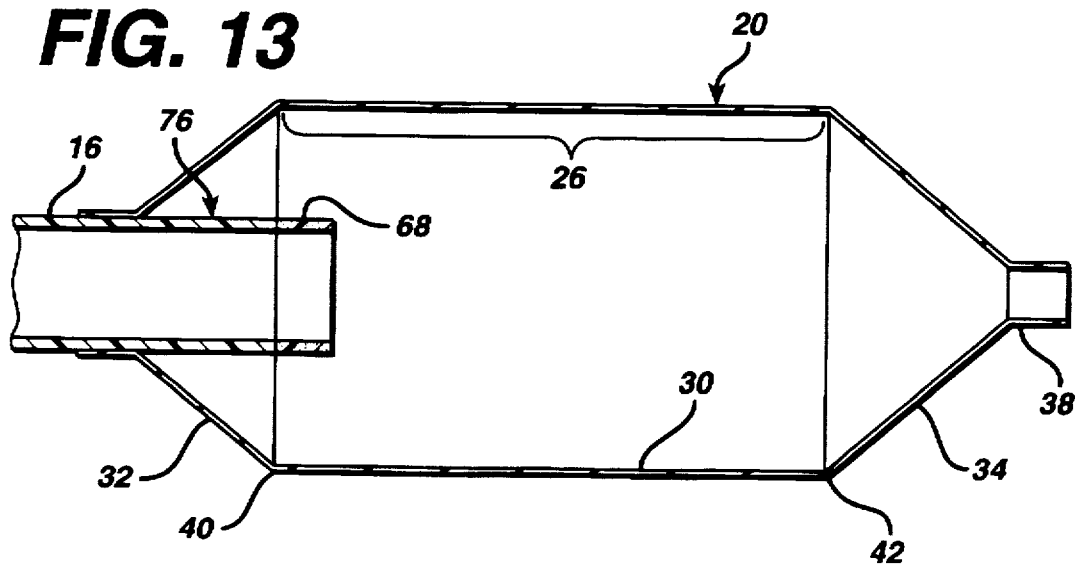
Figure 14:
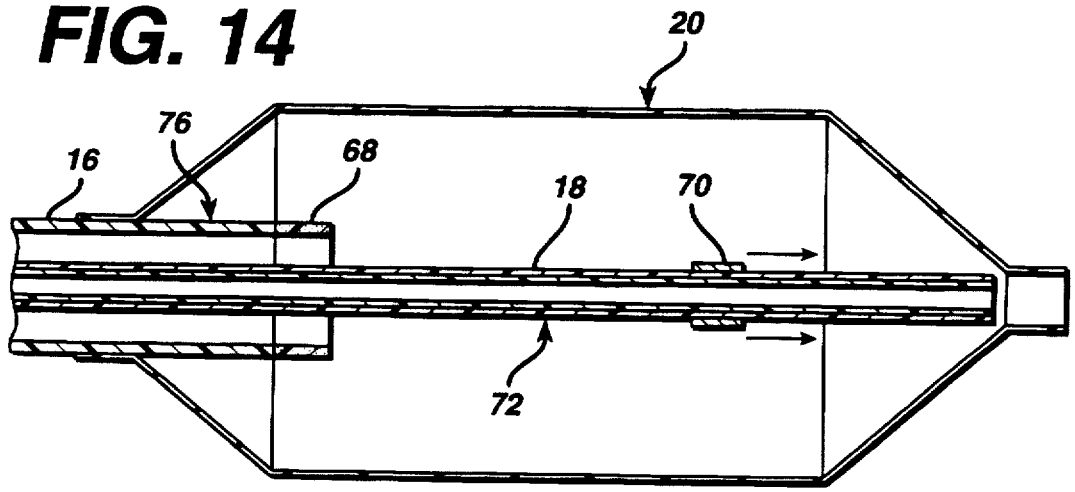

On the other hand, an exterior marker band 78 may be used to create a larger proximal shelf or annular surface, which may assist in advancing a stent 86 crimped over a deflated balloon 88, as shown in FIG. 10. This type of arrangement will resist a possible tendency of the stent 86 to slip in a proximal direction while the balloon catheter 80 is advanced to the desired position within a lesion or stenosis 66.

Figure 6:
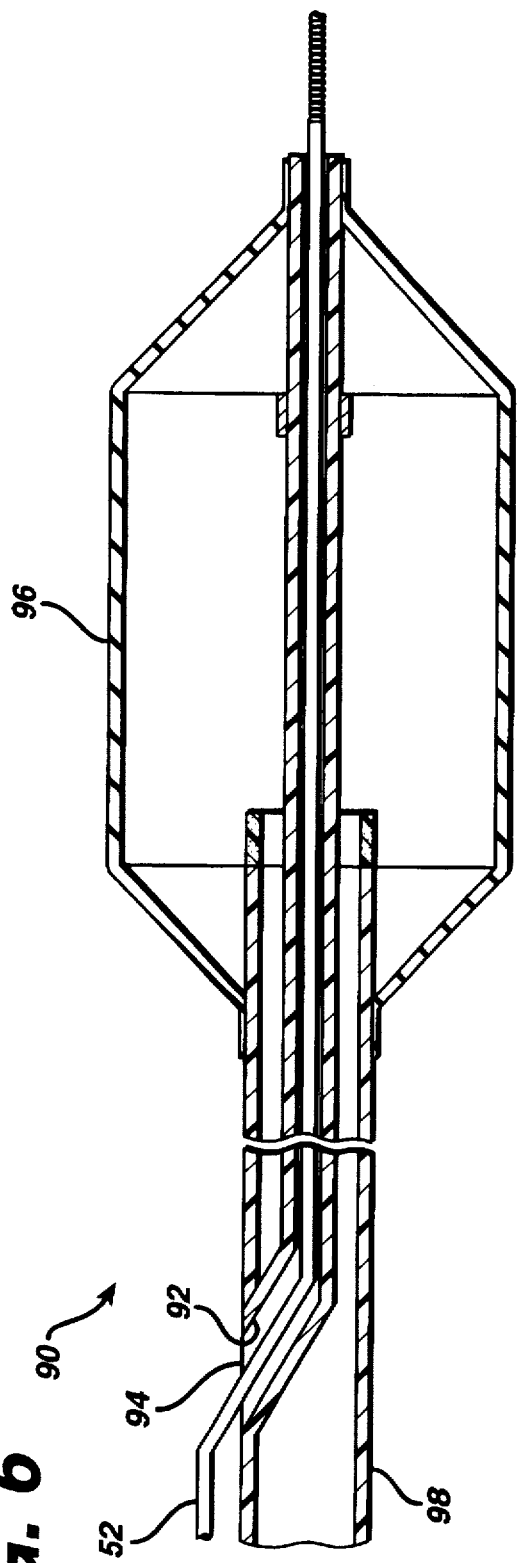
FIGS. 6–9 are partial cross-sectional views of alternative embodiments of the present invention.

In addition, it is often desirable to exchange a first balloon catheter that has been advanced over a guidewire 52 with a second balloon catheter, without dislodging the guidewire 52 from the treatment site. Accordingly, a balloon catheter 90 may be constructed in a rapid exchange configuration as illustrated in FIG. 6, wherein a guidewire lumen 92 extends from the distal tip of the catheter 90 only to a guidewire port 94 between the balloon 96 and the proximal end of the catheter 90. The guidewire 52 then extends proximally from the guidewire port 94, parallel and external to the catheter shaft 98.

Figure 7:
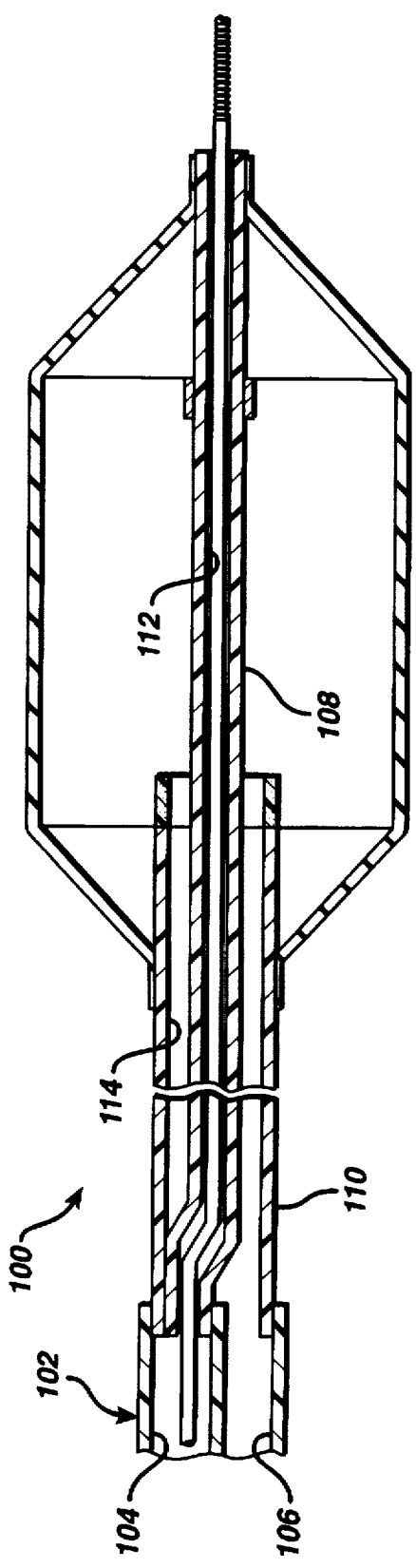

Alternatively, a balloon catheter 100 of the present invention may also be provided with "dual lumen" proximal shaft 102 as shown in FIG. 7, such that proximal shaft 102 is formed of a single extrusion defining both a proximal guidewire lumen 104 and a proximal inflation lumen 106, connected with inner and outer distal tubes 108 and 110 defining a distal guidewire lumen 112 and a distal inflation lumen 114, respectively.

Referring to FIG. 8, another embodiment of an intravascular balloon catheter 84 in accordance with this invention is disclosed. The balloon catheter inner shaft 118 may be constructed of multiple layers of plastic materials, such as by coextrusion or other extrusion processes. Similar processes are described in U.S. Pat. No. 5,063,018 to Fontirroche, which is commonly assigned with the present application, the disclosure of which is incorporated herein by reference. In accordance with the present invention, that extrusion process may be modified to coextrude inner shaft 118. Tube 118 is formed of an inner layer 120 plus an outer layer 122 which may be added by coextrusion, typically defining a lumen 124 through which a guidewire 52 may be inserted.

Likewise, the balloon 126 of the present balloon catheter 84 may be constructed of multiple layers 128 and 130, such as in FIG. 8. Such a multiple layer balloon 126 is disclosed in U.S. Pat. No. 5,290,306 to Trotta et al., entitled "Puncture Resistant Balloon Catheter," to Trotta, which is commonly assigned and incorporated herein by reference.

Figure 9:
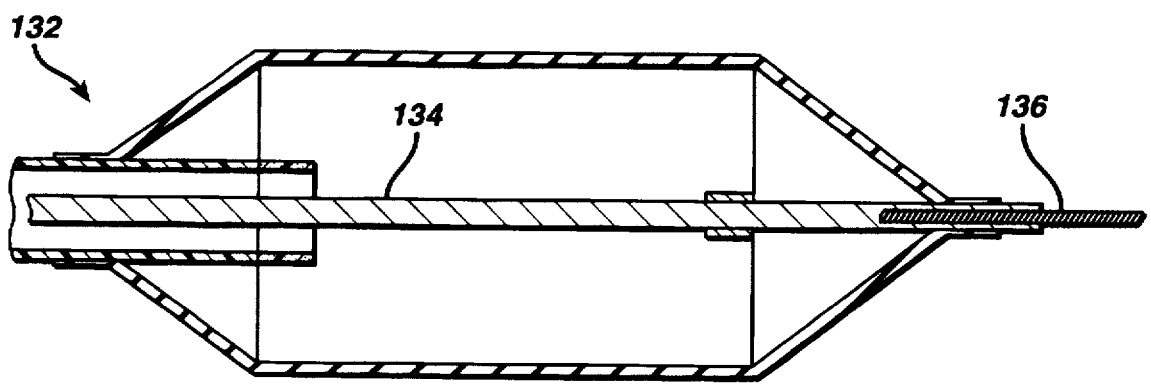

A fixed wire embodiment of the present invention is shown in FIG. 9, in which a balloon catheter 132 includes an inner shaft 134 defining no guidewire lumen. Rather, the inner shaft 134 is firmly affixed to a flexible wire 136 at the distal end of balloon catheter 132.

It should be understood that an unlimited number of configurations for the present invention can be realized. The foregoing discussion describes merely exemplary embodiments illustrating the principles of the present invention, the scope of which is recited in the following claims. Those skilled in the art will readily recognize from the description, claims, and drawings that numerous changes and modifications can be made without departing from the spirit and scope of the invention.

I claim:

1. An intravascular balloon catheter for treating a portion of the body of a patient, comprising:
   a flexible catheter shaft, at least a distal portion of the catheter shaft having an inner shaft member coaxially surrounded by an outer shaft member, an inflation lumen being defined by an annular space between said inner and outer shaft members;
   a flexible balloon disposed near a distal end of the catheter shaft, the balloon having a working portion with a constant cross-sectional area, a proximal end of the balloon being sealed to the outer shaft member, and a distal end of the balloon being sealed to the inner shaft member, whereby the inflation lumen is in fluid communication with the interior of the balloon; and
   first and second radiopaque markers disposed within the interior of the balloon, the first marker being affixed to the inner shaft member, and the second marker being affixed to the outer shaft member, said first and second markers being positioned at a distal and proximal end of the balloon working portion, respectively, whereby the first and second markers indicate under fluoroscopy the position of the balloon working portion within the body of the patient.

2. The intravascular balloon catheter as set forth in claim 1, wherein the balloon working portion has a cylindrical shape.

3. The intravascular balloon catheter as set forth in claim 2, the balloon further comprising a proximal and distal frusto-conical tapering segment, and proximal and distal legs being sealed to the outer and inner shaft members, respectively, wherein each of the first and second markers are longitudinally positioned at a transition between the cylindrical working portion and the distal and proximal tapering segments, respectively.

4. The intravascular balloon catheter as set forth in claim 1, wherein the balloon is formed of at least two layers of different materials.

5. The intravascular balloon catheter as set forth in claim 1, further comprising a flexible fixed wire affixed to the inner shaft member and extending distally beyond the distal end of the inner shaft member.

6. The intravascular balloon catheter as set forth in claim 1, wherein the balloon is formed of a substantially inelastic material.

7. The intravascular balloon catheter as set forth in claim 1, wherein the inner shaft member defines a guidewire lumen adapted to slidingly receive a guidewire extending from a proximal guidewire port that is proximal of the balloon to a distal guidewire port that is distal to the balloon.

8. The intravascular balloon catheter as set forth in claim 7, wherein the proximal guidewire port is disposed between a proximal end of the catheter shaft and the balloon, thereby enabling a guidewire to traverse a path from the distal guidewire port through the guidewire lumen defined by the inner shaft member, through the proximal guidewire port, and extend proximally along the exterior of a proximal portion of the catheter shaft in a rapid exchange configuration.

9. The intravascular balloon catheter as set forth in claim 7, wherein said catheter shaft further comprises a proximal shaft portion defining a proximal inflation lumen and a proximal guidewire lumen, the proximal inflation lumen communicating with an inflation lumen defined by an annular space between the outer and inner shaft members, and the proximal guidewire lumen extending parallel to the proximal inflation lumen and communicating with the guidewire lumen.

10. The intravascular balloon catheter as set forth in claim 7, wherein said inner shaft member is formed of at least two layers of different materials, the innermost layer defining the guidewire lumen and being more lubricious to facilitate movement of a guidewire within the guidewire lumen.

11. The intravascular balloon catheter as set forth in claim 1, wherein inner and outer shaft members are each formed of plastic, and the first and second markers are formed of metal.

12. An intravascular balloon catheter for treating a portion of the body of a patient, comprising:

a flexible catheter shaft, at least a distal portion of the catheter shaft having an inner shaft member coaxially surrounded by an outer shaft member, an inflation lumen being defined by an annular space between said inner and outer shaft members;

a flexible balloon disposed near a distal end of the catheter shaft, a proximal end of the balloon being sealed to the outer shaft member, and a distal end of the balloon being sealed to the inner shaft member, whereby the inflation lumen is in fluid communication with the interior of the balloon; and first and second radiopaque markers disposed within the interior of the balloon, the first marker being affixed to the inner shaft member, and the second marker being affixed to the outer shaft member, whereby the first and second markers indicate under fluoroscopy the position of the balloon within the body of the patient, wherein the second marker is formed by a plastic ring containing a radiopaque agent and affixed to a distal end of said outer shaft member.

13. The intravascular balloon catheter as set forth in claim 12, wherein a percentage concentration of said radiopaque agent is predetermined, such that said first and second markers have equal fluoroscopic brightness.

14. The intravascular balloon catheter as set forth in claim 12, wherein the second marker has the same outer diameter as said outer shaft member.

15. An intravascular balloon catheter, comprising:

a first tube of flexible plastic defining a guidewire lumen, said first tube being formed of an outer plastic layer and an inner plastic layer, the plastic materials of said outer and inner plastic layers being different and bonded to each other, said guidewire lumen being adapted to slidingly receive a guidewire, said inner plastic layer exhibiting a more lubricious surface than said outer plastic layer;

a second flexible plastic tube surrounding said first tube and defining an inflation lumen between the outer surface of the first tube and the inner surface of the second tube;

a flexible balloon having a distal end coupled to said first tube and a proximal end coupled to said second tube, such that the interior volume of the balloon is in fluid communication with said inflation lumen; and first and second radiopaque markers affixed to the first and second tube, respectively.

16. The intravascular balloon catheter as set forth in claim 15, in which the material of the outer plastic layer has greater stiffness than the material of the inner plastic layer.

17. The intravascular balloon catheter as set forth in claim 15, in which the material of said outer plastic layer is selected from the group consisting of nylon, polyurethane, and polyester.

18. The intravascular balloon catheter as set forth in claim 15, wherein the balloon defines a working length, said first and second markers being positioned at a distal and proximal end of the working length, respectively.

19. The intravascular balloon catheter as set forth in claim 15, wherein the balloon is formed of a substantially inelastic material.

20. The intravascular balloon catheter as set forth in claim 15, further comprising a distal guidewire port that is distal to the balloon and a proximal guidewire port that is between the balloon and a proximal end of the second tube, thereby enabling a guidewire to traverse a path from the distal guidewire port through the guidewire lumen, through the proximal guidewire port, and extend proximally along the exterior of a proximal portion of the catheter shaft in a rapid exchange configuration.

21. The intravascular balloon catheter as set forth in claim 20, wherein the second marker has the same outer diameter as said second shaft member.

22. The intravascular balloon catheter as set forth in claim 15, wherein the second marker is formed by a plastic ring containing a radiopaque agent and affixed to a distal end of said second shaft member.

23. The intravascular balloon catheter as set forth in claim 15, wherein inner and outer shaft members are each formed of plastic, and the first and second markers are formed of metal.

24. An intravascular balloon catheter for expanding a stent within the body of a patient, comprising:

a flexible catheter shaft, at least a distal portion of the catheter shaft having an inner shaft member coaxially surrounded by an outer shaft member;

a flexible balloon disposed near a distal end of the catheter shaft, a proximal end of the balloon being sealed to the outer shaft member, and a distal end of the balloon being sealed to the inner shaft member;

first and second radiopaque markers disposed within the interior of the balloon, the first marker being affixed to the inner shaft member, and the second marker being affixed to a distal end of the outer shaft member, an outer diameter of the second inner marker being larger than an outer diameter of the outer shaft member, thereby forming an annular shelf;

a stent assembled in a crimped configuration around the balloon in an uninflated state, whereby the balloon is adapted to inflate and expand the stent within the desired site, said annular shelf engaging a proximal end of the stent to resist proximal motion of the stent relative to the catheter shaft as the balloon catheter is advanced within the body of the patient.

25. The intravascular balloon catheter as set forth in claim 24, wherein the balloon defines a working length, said first and second markers being positioned at a distal and proximal end of the working length, respectively.

26. The intravascular balloon catheter as set forth in claim 24, wherein the inner shaft member defines a guidewire lumen adapted to slidingly receive a guidewire extending from a proximal guidewire port that is proximal of the balloon to a distal guidewire port that is distal to the balloon.

27. The intravascular balloon catheter as set forth in claim 26, wherein the proximal guidewire port is disposed between a proximal end of the catheter shaft and the balloon, thereby enabling a guidewire to traverse a path from the distal guidewire port through the guidewire lumen defined by the inner shaft member, through the proximal guidewire port, and extend proximally along the exterior of a proximal portion of the catheter shaft in a rapid exchange configuration.

28. A method of making an intravascular balloon catheter for treating a portion of the body of a patient, comprising the steps of:

provinding an outer and inner shaft member, the outer shaft member being a tube defining a lumen having an inner diameter that is large enough to accept the inner shaft member within said lumen;

affixing distal and proximal radiopaque markers to the inner and outer shaft members, respectively;

providing a flexible balloon having a central substantially cylindrical portion, and a proximal and distal tapering segment;

sealing a proximal end of the balloon to the outer shaft member, such that the proximal marker is longitudinally aligned with a proximal transition between the central portion and the proximal tapering segment;

inserting the inner shaft member within the lumen of the outer shaft member and longitudinally aligning the distal marker with a distal transition between the central portion and the distal tapering segment; and sealing a distal end of the balloon to the inner shaft member while the distal marker and the distal transition are so aligned.

29. The method of claim 28, further comprising the additional step of sealing the proximal ends of the inner and outer shaft members, to resist relative movement thereof.

30. The method of claim 28, further comprising the additional step of forming the proximal marker of a plastic formulation having a radiopaque agent.

31. The method of claim 28, wherein said step of providing the inner shaft member further comprises coextruding the inner shaft member into a tube defining a lubricious guidewire lumen.

* * * * *